United States Patent [19]
Starke et al.

[11] Patent Number: 5,147,341
[45] Date of Patent: Sep. 15, 1992

[54] SELF CONTAINED URINARY CATHETER ASSEMBLY

[76] Inventors: Richard N. Starke, 1718 Arrowhead Trail NE, Atlanta, Ga. 30345; Raymond G. Bigler, 1771 Wesley Way, Conyers, Ga. 30207

[21] Appl. No.: 664,873

[22] Filed: Mar. 5, 1991

[51] Int. Cl.$^5$ .............................................. A61F 5/44
[52] U.S. Cl. ..................................... 604/349; 604/352
[58] Field of Search ................ 604/331, 349, 350–352; 428/760, 761, 768; 4/144.1–144.4

[56] References Cited

U.S. PATENT DOCUMENTS 4,246,909  1/1981  Wu et al. ............................. 128/768
4,652,259  3/1987  O'Neil .

FOREIGN PATENT DOCUMENTS 2181951  5/1987  United Kingdom .

Primary Examiner—Randall L. Green
Assistant Examiner—R. Clarke
Attorney, Agent, or Firm—B. J. Powell

[57] ABSTRACT

A self contained urinary catheter assembly for use in draining the bladder through the urethra comprising a flexible receptacle defining a closed chamber therein; a mounting on the receptacle with a catheter opening therethrough to the closed chamber; and a catheter carried in the closed chamber in the flexible receptacle to be selectively extended out of the chamber through the catheter opening during use and retracted after use. The catheter may be selectively released from the chamber and opening so that uncontaminated urine samples may be removed from the closed chamber.

14 Claims, 3 Drawing Sheets

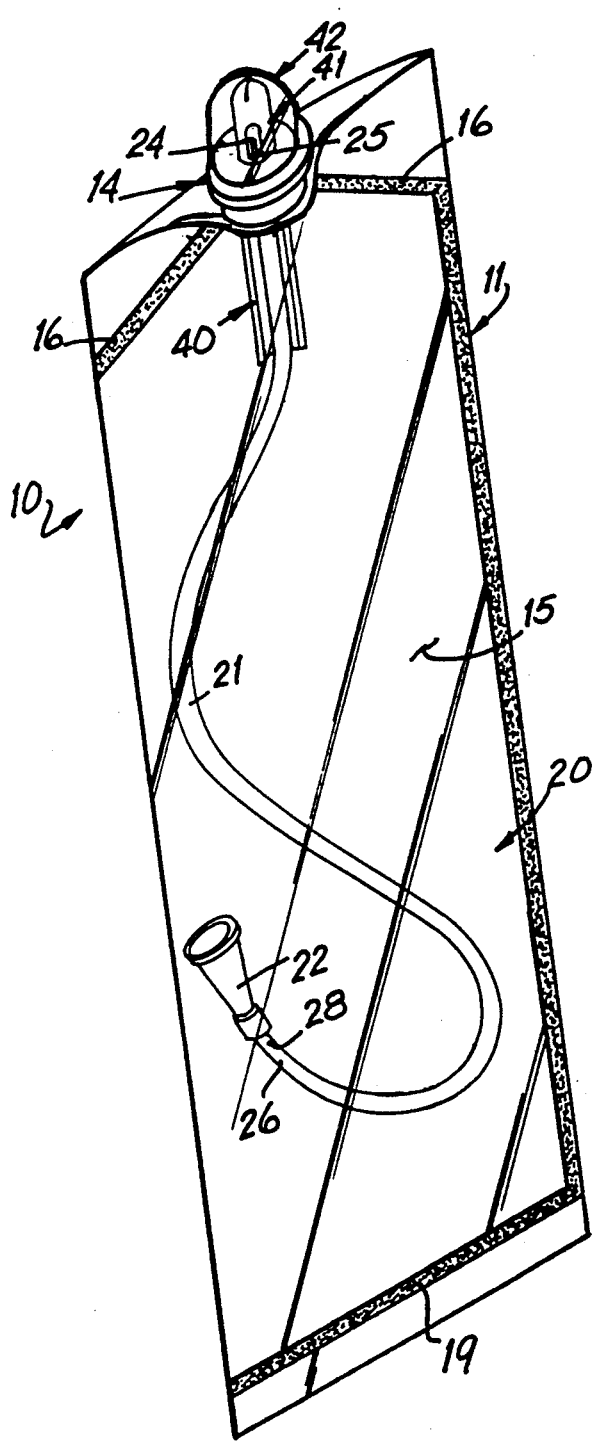
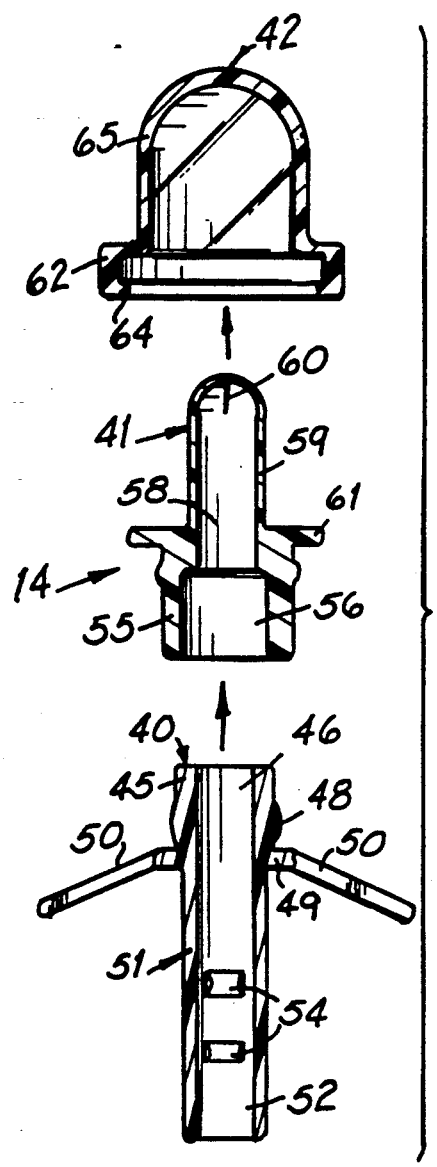
FIG 1
FIG 2

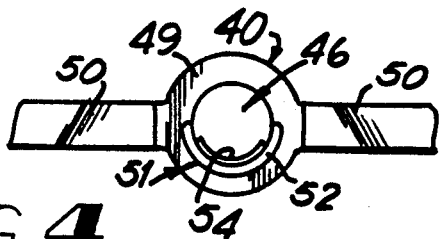
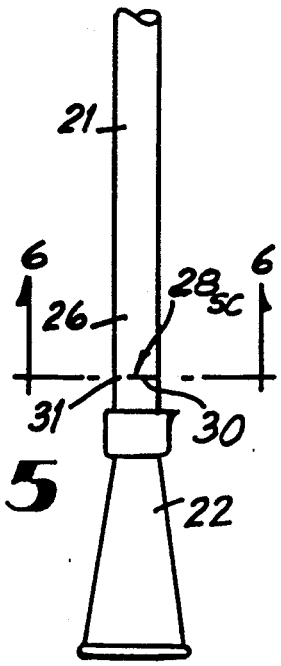
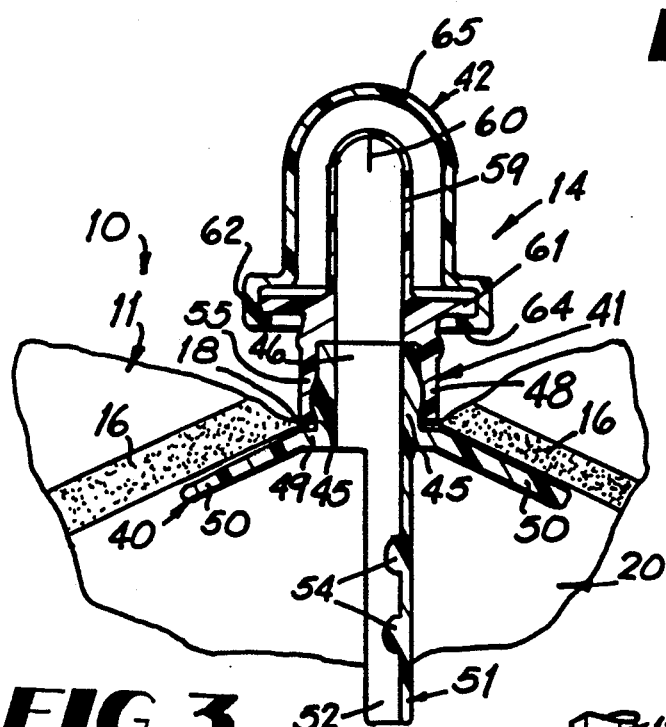
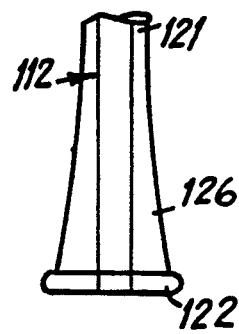
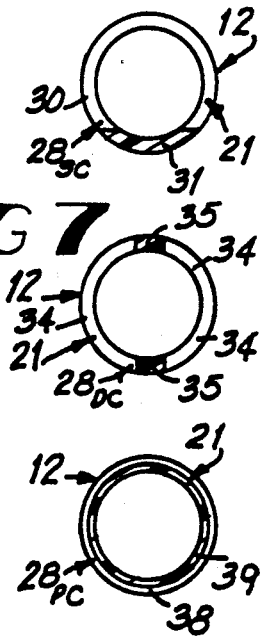

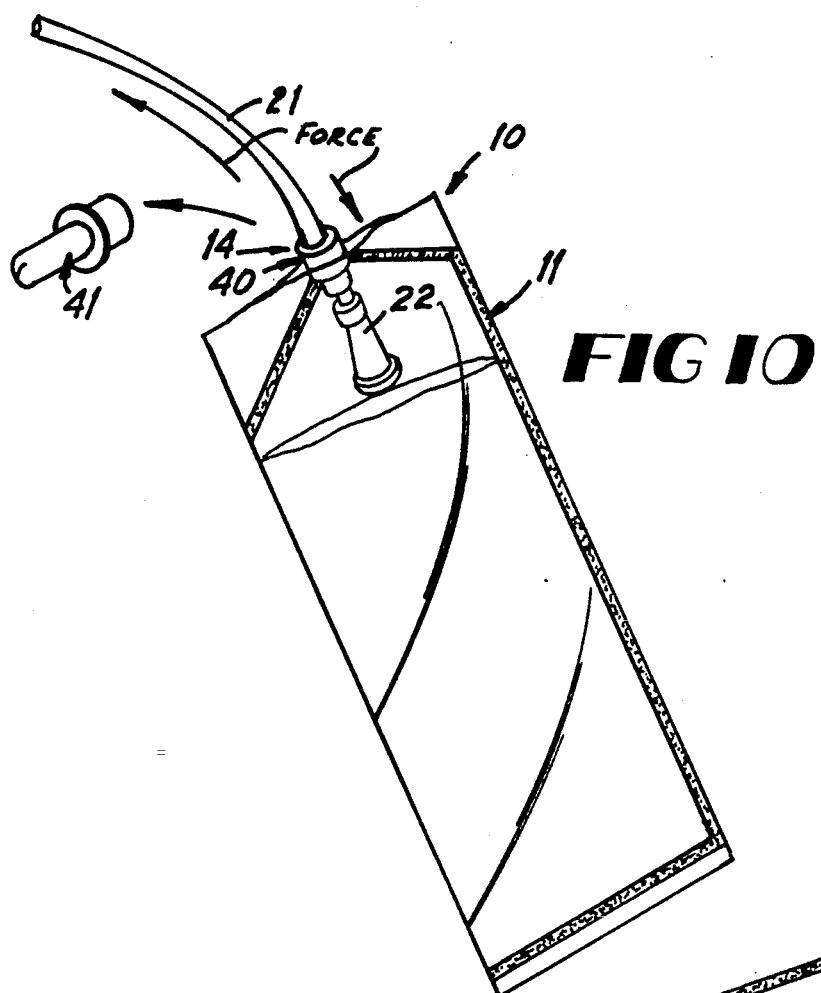
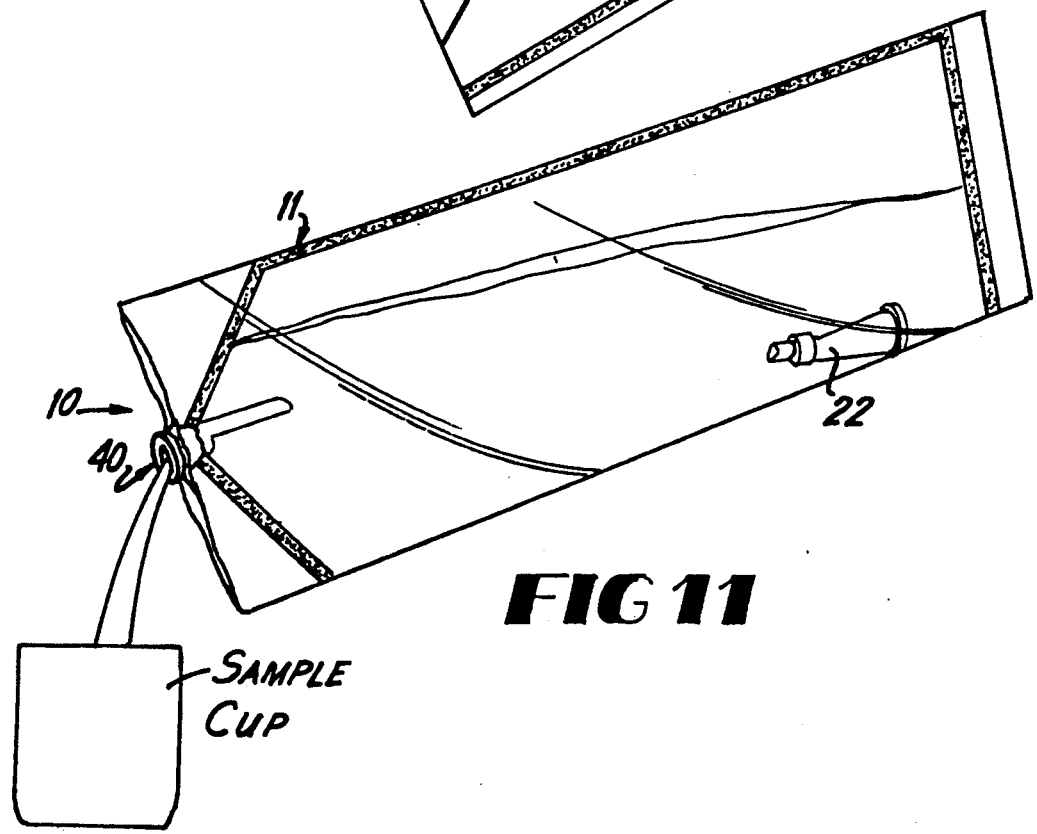

SELF CONTAINED URINARY CATHETER ASSEMBLY

BACKGROUND OF THE INVENTION

This invention relates generally to catheters and more particularly to intermittent catheter assemblies incorporated in a dual purpose sterile receptacle.

Self contained urinary catheter assemblies are currently available. These self contained catheters are available with the catheter itself stowed in a flexible bag to remain in a sterile field. An introducer is mounted on the bag to catheter to be extended from the bag during use and retracted into the bag again after use. While the catheter is not extended, the introducer is covered by a sealing cover. Since the discharge end of the catheter always remains in the bag, the bag is sized to serve as a urine receptacle when the catheter is inserted through the urethra and into the bladder. These catheter assemblies typically are intermittently used only when the bladder needs to be drained and are removed after each use for disposal. The catheter/introducer assembly is the subject of U.S. Pat. No. 4,652,259, dated Mar. 24, 1987, issued to Alexander G. B. O'Neil.

One of the problems with these prior art self contained catheter assemblies is that it is difficult to obtain an uncontaminated sample from the bag for testing as is frequently required in the environment in which the assembly is used. Another problem is that it is sometimes difficult to grip the catheter through the bag and the introducer to manipulate the catheter as it is being inserted in or removed from the urethra.

SUMMARY OF THE INVENTION

These and other problems and disadvantages associated with the prior art are overcome by the invention disclosed herein by providing a self contained urinary catheter assembly which provides a simple method of obtaining an uncontaminated urine sample for testing. The invention further provides means for gripping the catheter through the receptacle so that manipulation of the catheter with respect to the receptacle during use is facilitated.

The apparatus of the invention includes a flexible receptacle defining a closed chamber with a catheter carried in the closed chamber and mounting means on the flexible receptacle defining a catheter opening therethrough into said closed chamber through which said projecting end of the catheter can extend for insertion into the bladder through the urethra. The catheter has arresting means on one end thereof to prevent inadvertent removal of the catheter from the receptacle but which is constructed to release the catheter from the receptacle when a sufficient force is exerted on the catheter so that uncontaminated samples can be poured from the receptacle. The mounting means is provided with a guide flange projecting into the chamber in the receptacle and in registration with said catheter opening. The guide flange has an arcuate cross-sectional shape conforming generally to a portion of the cross-sectional shape of the catheter tube so that the projecting end of the catheter can be laid in the guide flange to align the catheter with the catheter opening through the mounting means. Further, gripping means to positively engage the catheter when it is pressed against the gripping means permits the catheter to be selective fixed with respect to the mounting means while the catheter and receptacle are being manipulated.

These and other features and advantages of the invention will become more clearly understood upon consideration of the following detailed description and accompanying drawings wherein like characters of reference designate corresponding parts throughout the several views and in which:

BRIEF DESCRIPTION OF THE DRAWINGS

FIG. 1 is a perspective view of a self contained urinary catheter assembly embodying the invention;

FIG. 2 is an enlarged exploded view shown in quarter section of the introducer subassembly;

FIG. 3 is an enlarged axial cross-sectional view of the introducer portion of the assembly installed with the protective cover in place and the catheter in its stowed position;

FIG. 4 is an end view of the introducer assembly showing the guide means;

FIG. 5 is an enlarged side view of the discharge end portion of the catheter showing the weakened section therein;

FIG. 6 is an enlarged cross-sectional view taken along line 6—6 in FIG. 5;

FIG. 7 is a view similar to FIG. 6 showing a second embodiment of the weakened section in the catheter;

FIG. 8 is a view similar to FIG. 6 showing a third embodiment of the weakened section in the catheter;

FIG. 9 is an enlarged side view, partly in cross-section, of the discharge end portion of the catheter showing an alternate release means; and FIGS. 10 and 11 illustrate the invention being used to obtain an uncontaminated urine sample for testing.

These figures and the following detailed description disclose specific embodiments of the invention, however, it is to be understood that the inventive concept is not limited thereto since it may be embodied in other forms.

DETAILED DESCRIPTION OF ILLUSTRATIVE EMBODIMENTS

Referring to FIG. 1, it will be seen that the self contained urinary catheter assembly 10 includes a flexible receptacle 11 which carries a catheter 12 therein. An introducer assembly 14 maintains the catheter 12 in a sterile field as it is stowed in the receptacle 11 and also serves to isolate the catheter as it is inserted in the urethra to minimize urethra and bladder infection induced by the use of the catheter.

The receptacle 11 serves to stow the catheter 12 in a sterile environment until it is used. It then serves as a fluid reservoir into which the bladder is drained and finally serves to again stow the catheter 12 until the assembly 10 can be discarded.

The receptacle 11 has a thin tubular side wall 15 which is seamed from a single sheet of transparent plastic material. The top end of the side wall 15 is partly closed by a pair of angled top seams 16 that angle upwardly and inwardly in a general chevron shape. An access opening 18 is left between the upper inner ends of the seams 16 to mount the introducer assembly 14 therein. A bottom seam 19 closes the opposite end of the side wall 15 to form a closed chamber 20 in the receptacle 11.

The catheter 12 includes a catheter tube 21 with an enlarged arresting member 22 at the drainage end of the catheter tube 21. The drainage tube 21 has a conventional drainage passage along the length thereof which is closed off at the rounded tip in the projecting end 24 of the tube 21 with inlet openings 25 as is conventional. The drainage end 26 of the tube 21 is connected to the enlarged arresting member 22. The arresting member 22 is illustrated in FIGS. 1-8 as a conventional syringe connection.

To permit the catheter 12 to be released from the receptacle 11, a release means is provided in the catheter tube 21 to permit the arresting member 22 to be removed and allow the tube 21 to be withdrawn from the receptacle 11 and introducer assembly 14. FIGS. 5-8 illustrate the release means as a weakened section 28 in the catheter side wall 29 adjacent the arresting member 22 which causes the side wall 29 to break when a force above a prescribed threshold level pulls the arresting member and the catheter tube apart. The threshold level of force is selected to be substantially above that to which the side wall 29 of the catheter 12 is subjected while the assembly 10 is in normal use but personnel can pull on the catheter tube 21 with enough force to cause the side wall 29 to separate at the weakened section 28. It has been found that leaving about 25-40% of the catheter side wall 29 uncut performs satisfactorily.

FIGS. 5 and 6 illustrate the weakened section 28 being formed with a single cut 30 in the catheter side wall 29. For sake of clarity, the single cut weakened section has been designated as $28_{SC}$. The uncut portion 31 of the side wall 29 complies with the criteria set forth above. When the technician pulls on the catheter side wall 29 lying outside the receptacle 11, the uncut portion 31 is broken to release the arresting member 22 from the catheter tube 21 thereby allowing it to pass out of the introducer assembly 14 as will become more apparent.

FIG. 7 illustrates a second embodiment of the weakened section 28 which has been designated $28_{DC}$. The section $28_{DC}$ has been formed by making two cuts 34 in opposition to each other in the side wall leaving two opposed uncut sections 35 therebetween conforming to the parameters set forth above. The section $28_{DC}$ operates similarly to that associated with the single cut.

FIG. 8 illustrates yet another embodiment of the weakened section which has been designated $28_{PC}$. The section $28_{PC}$ is formed by making a peripherally extending cut 38 around the periphery of the catheter side wall 29 to leave a continuous uncut section 39 adjacent the drainage passage through the catheter tube 21. The uncut section 39 is sized to conform to the parameters set forth above.

From the above, it will be seen that pulling on the catheter tube 21 projecting out of the introducer assembly 14 will cause a separating force across the weakened section 28 in the tube 21 thereby causing it to separate and release the enlarged arresting member 22 from the end of the catheter tube 21. This allows the catheter tube 21 to pass out through the introducer assembly 14 while the arresting member 22 drops within the close chamber 20 in the receptacle 11.

The introducer assembly 14 includes generally a mounting member 40 adapted to be mounted in the opening 18 in the flexible receptacle 11 and disposed within the chamber 20 in the receptacle 11. The urethra penetrating protective member 41 engages the mounting member 40 to lock the receptacle 11 around the mounting member 40 while at the same time providing a penetrating isolation cover to penetrate the distal end of the urethra during use. A stowing cover 42 is removably mounted over the projecting portion of the urethra penetrating protective member 41 to cover it when it is not in use. The urethra penetrating protective member 21 is used in accordance with the teachings of U.S. Pat. No. 4,652,259, which description is incorporated herein by reference.

The mounting member 40 comprises generally a cylindrical bag support section 45 which fits through the opening 18 between the top seams 16 in the receptacle and which defines a catheter passage 46 therethrough sized to just receive the catheter tube 21. The outside surface of the support section 45 is provided with a locking bulge 48 that helps hold the urethra penetrating protective member 41 in place as will become more apparent. The base of the support section 45 is provided with a stop flange section 49 which projects outwardly therefrom and serves to arrest the movement of the mounting member 40 out of the interior of the chamber 20 in the receptacle 11. The flange section 49 is provided with a pair of angled orienting extensions 50 which engage the interior of the receptacle 11 along the top seam 16 to properly orient the mounting member 40 with respect to the receptacle 11 and provide additional support to prevent the mounting member 40 from being pulled out of the receptacle 11.

Mounted on and depending below the stop flange section 49 is a catheter gripping guide 51. The guide 51 is used to guide the tip of the catheter 12 into the catheter opening in the section 45. It is also used to assist in gripping the catheter tube 21 to fix the catheter 12 with respect to the mounting member 40 to facilitate the using of the catheter 12 and to facilitate its extension from and retraction into the chamber 20 in the receptacle 11. The gripping guide 51 includes a flange 52 projecting below the flange section 48 with an inside radius of curvature corresponding generally to the outside radius of the catheter tube 21. The arcuate flange 52 has a semi-circular cross sectional shape so that one side of the flange is open and provides an elongate recess into which the projecting end 24 of the catheter 12 can be placed. The flange 52 is oriented in registration with the catheter passage 46 so that the projecting end 24 of the tube 21 will be guided into the passage 46. To facilitate gripping the catheter 12 located inside the receptacle 11, a plurality of grippers 54 are provided on the gripping guide 51 and project inwardly thereof. The grippers 54 are designed to engage the outside surface of the catheter tube 21 as it is pressed thereagainst to help fix the catheter tube 21 with respect to the flange 52 and thus the mounting member 40.

The urethra penetrating protective member 41 is made out of a soft material such as silicone or latex rubber. The urethra penetrating protective member 41 includes a cylindrical base 55 which defines a mounting counterbore 56 in one end thereof sized to fit over the cylindrical section 45 of the mounting member 40 and be frictionally retained thereon to hold the receptacle onto the mounting member 40. The cylindrical base 55 is also provided with catheter passage 58 corresponding in size to the catheter passage 46 in the mounting member 40 so that the catheter tube 21 can also pass through the catheter passage 58. That end of the cylindrical base 55 opposite the counterbore 56 mounts a penetrating cover 59 which projects out from the mounting member 40 when the protective member 41 is in place. The projecting end of the penetrating cover 59 is cross cut as indicated at 60 so that the penetrating cover 59 can extend beyond the periurethral area in the urethra so as to bypass the area with the high bacterial count during use. As explained in U.S. Pat. No. 4,652,259, this allows the projecting end 24 of the catheter tube 21 to pass beyond the periurethral area and thus reduce the bacterial infection associated with the use of the catheter. An annular holding flange 61 is provided around the base of the penetrating cover 59 at the cylindrical base 55 which purpose is to arrest the movement into the urethra and to hold the stowing cover 42 in place as will become more apparent.

The stowing cover 42 comprises generally an annular mounting flange 62 which has a diameter large enough to extend over the annular holding flange 61 on the protective member 41 and is provided with an inwardly directed annular lip 64 which extends under the holding flange 61 to hold the stowing cover 42 in place over the end of the protective member 41. An enclosure dome 65 is provided on the mounting flange 62 which projects out and over the projecting end of the penetrating cover 59 to enclose it. Thus, when the stowing cover 42 is in place, a sterile field is defined completely around the catheter 12 and the penetrating cover 59 on the urethra penetrating member 41 to provide a sterile field to which the patient is exposed.

As best seen in FIG. 1, the self contained urinary catheter assembly 10 comes assembled with the stowing cover 42 in place on the introducer assembly 14 and with the catheter 12 stowed in the chamber 20 on the flexible receptacle 11. The user removes the stowing cover 42 and uses the assembly 10 in conventional manner to drain the user's bladder. After using the assembly 10, the catheter 12 can again be stowed in the chamber 20 and the stowing cover 42 replaced on the introducer assembly 14 to again close the chamber 20. The user can then dispose of the entire unit.

Where it is desirable to take an uncontaminated sample of the urine drained, the technician extends the catheter tube 21 and pulls on the catheter tube externally of the introducer assembly 14 so as to pull the enlarged arresting member 22 up against the bottom of the mounting member 40 as seen in FIG. 10. By continuing to pull on the catheter tube 21, the catheter tube 21 breaks at the weakened section 28 to release the catheter tube 21 from the passages 46 and 58 in the introducer assembly 14. The technician then removes the urethra penetrating protective member 41 from the mounting member 40 as seen in FIG. 10. The technician can then simply pour a urine sample for testing out through the mounting member 40 as seen in FIG. 11. Since this sample is not exposed to any external contamination, the sample obtained is an uncontaminated sample for testing.

The release means described above is directed to weakened section 28 being formed in the catheter tube 21. It will be understood that different type release means could be used. For instance, making an enlarged section 122 in the drainage end 126 of the catheter 112 seen in FIG. 9 will allow the enlarged section 122 to stop the catheter tube 121 from being pulled out of the mounting member 40 during normal usage. The enlarged member 122 is made out of a material and sized such that, when the threshold force is exceeded, the arresting member 122 will collapse and allow the end of the catheter 112 to pass out through the passage 46 in the mounting member 40.

What is claimed as invention is:

1. A self contained urinary catheter assembly for use in draining the bladder through the urethra comprising:

a) a flexible receptacle defining a closed chamber therein;
   b) a catheter carried in said closed chamber in said flexible receptacle and including:
      b1) an elongate catheter tube defining a projecting end and a drainage end at opposite ends thereof and defining a drainage passage extending from said projecting end to said drainage end so that fluids in the bladder can drain therethrough when said projecting end of said catheter tube is inserted into the bladder through the urethra,
      b2) arresting means at said drainage end of said catheter tube and
      b3) release means for selectively releasing said arresting means from said catheter tube; and,
   c) mounting means mounted on said flexible receptacle and defining a catheter opening therethrough into said closed chamber through which said projecting end of said catheter tube can extend for insertion into the bladder through the urethra, said catheter opening configurated so as to prevent said drainage end of said catheter tube from passing therethrough until said release means releases said arresting means from said catheter tube.

2. The self contained urinary catheter assembly of claim 1 wherein said release means includes a weakened section in said catheter tube adjacent said arresting means that breaks when that portion of said catheter tube projecting out of said mountings is pulled with a force greater than any force to which said catheter tube is subjected during normal urinary drainage use so that said catheter tube can be pulled out of said receptacle leaving said catheter opening open to pour a non contaminated sample therethrough while said arresting means remains in said closed chamber in said receptacle.

3. The self contained urinary catheter assembly of claim 2 wherein said weakened section in said catheter tube includes at least one cut made through a major portion of the cross sectional area of said catheter tube so that said catheter tube breaks at said cut when pulled with sufficient force.

4. The self contained urinary catheter assembly of claim 2 wherein said weakened section in said catheter tube includes a plurality of cuts made through the cross sectional area of said catheter tube so that a major portion of the cross-sectional area of said catheter tube is cut whereby said catheter tube breaks at said cuts when pulled with sufficient force.

5. The self contained urinary catheter assembly of claim 2 wherein said weakened section in said catheter tube includes a peripherally extending cut made in said catheter tube so that a major portion of the cross sectional area of said catheter tube is cut so that said catheter tube breaks at said cut when pulled with sufficient force.

6. The self contained urinary catheter assembly of claim 1 wherein said mounting means includes orienting means for orienting said mounting means in said flexible receptacle.

7. The self contained urinary catheter assembly of claim 1 wherein said mounting means includes guide means for assisting in guiding said projecting end of said catheter tube into said catheter opening through said mounting means to permit said catheter to project from said flexible receptacle.

8. The self contained urinary catheter assembly of claim 7 wherein said guide means includes a guide flange projecting into said closed chamber, said guide flange in registration with said catheter opening and having an arcuate cross-sectional shape conforming generally to a portion of the cross-sectional shape of said catheter tube so that said projecting end of said catheter tube can be laid in said guide flange to align said catheter with said catheter opening through said mounting means.

9. The self contained urinary catheter assembly of claim 8 further including gripping means to positively engage said catheter tube when said catheter is pressed against said gripping means to permit said catheter to be selectively fixed with respect to said mounting means while said catheter and said receptacle are being manipulated.

10. The self contained urinary catheter assembly of claim 1 further including a urethra penetrating protective member covering said catheter opening, said protective member having a self closing projecting end thereon adapted to be positioned into the discharge end of the user's urethra to isolate bacteria from said catheter and through which said catheter passes as said catheter is being used.

11. A self contained urinary catheter assembly for use in draining the bladder through the urethra comprising:
   a) a flexible receptacle defining a closed chamber therein;
   b) a catheter carried in said closed chamber in said flexible receptacle defining a projecting end and a drainage end at opposite ends thereof and defining a drainage passage extending from said projecting end to said drainage end so that fluids in the bladder can drain therethrough when said projecting end of said catheter is inserted into the bladder through the urethra; and
   c) mounting means mounted on said flexible receptacle and defining a catheter opening therethrough into said closed chamber through which said projecting end of said catheter can extend for insertion into the bladder through the urethra, said mounting means including gripping means located at a position fixed relative to said catheter opening for gripping said catheter in said flexible receptacle when said catheter is pressed thereagainst to selectively arrest the movement of said catheter relative to said catheter opening.

12. A self contained urinary catheter assembly for use in draining the bladder through the urethra comprising:
   a) a flexible receptacle defining a closed chamber therein;
   b) a catheter carried in said closed chamber in said flexible receptacle defining a projecting end and a drainage end at opposite ends thereof and defining a drainage passage extending from said projecting end to said drainage end so that fluids in the bladder can drain therethrough when said projecting end of said catheter is inserted into the bladder through the urethra;
   c) mounting means mounted on said flexible receptacle and defining a catheter opening therethrough into said closed chamber through which said projecting end of said catheter can extend for insertion into the bladder through the urethra, said mounting means including guide means for assisting in guiding said projecting end of said catheter into said catheter opening through said mounting means to permit said catheter to project from said flexible receptacle, said guide means including a guide flange projecting into said closed chamber, said guide flange in registration with said catheter opening and having an arcuate cross-sectional shape conforming generally to a portion of the cross-sectional shape of said catheter tube so that said projecting end of said catheter tube can be laid in said guide flange to align said catheter with said catheter opening through said mounting means; and
   d) gripping means to positively engage said catheter when said catheter is pressed against said gripping means to permit said catheter to be selectively fixed with respect to said mounting means while said catheter and said receptacle are being manipulated.

13. The self contained urinary catheter assembly of claim 12 further including a urethra penetrating protective member covering said catheter opening said protective member having a self closing projecting end thereon adapted to be positioned into the discharge end of the user's urethra to isolate bacteria from said catheter and through which said catheter passes as said catheter is being used.

14. A self contained urinary catheter assembly for use in draining the bladder through the urethra comprising:
   a) a flexible receptacle defining a closed chamber therein and defining a catheter opening therethrough into said closed chamber;
   b) a catheter carried in said closed chamber in said flexible receptacle and including:
     b1) an elongate catheter tube defining a projecting end and a drainage end at opposite ends thereof and defining a drainage passage extending from said projecting end to said drainage end so that fluids in the bladder can drain therethrough when said projecting end of said catheter tube passes out of said closed chamber through said catheter opening and is inserted into the bladder through the urethra, and
     b2) arresting means at said drainage end of said catheter tube for preventing passage of said discharge end of said catheter out of said closed chamber through said catheter opening when the removal force is below a prescribed threshold force level and for permitting said drainage end of said catheter to pass out through said catheter opening when said prescribed threshold force level is exceeded.

* * * * *